United States Patent [19]

St. Pierre et al.

[11] Patent Number: 5,374,422

[45] Date of Patent: *Dec. 20, 1994

[54] INGESTIBLE [HYDROPHOBIC] POLYMERIC AMINES USEFUL FOR LOWERING BLOOD CHOLESTEROL

[75] Inventors: Leon E. St. Pierre, Frelighsburg; George R. Brown, Dollard-des-Ormeaux; Gaoming Wu, Montreal, all of Canada

[73] Assignee: Lowchol Scientific, Inc., Frelighsburg, Canada

[*] Notice: The portion of the term of this patent subsequent to Nov. 22, 2011 has been disclaimed.

[21] Appl. No.: 674,150

[22] Filed: Mar. 25, 1991

Related U.S. Application Data

[63] Continuation-in-part of Ser. No. 381,988, Jul. 19, 1989, Pat. No. 5,236,701.

[51] Int. Cl.$^5$ .................... A61K 31/74; L08F 112/08
[52] U.S. Cl. .......................... 424/78.12; 424/78.16
[58] Field of Search ............... 424/78.1, 78.16, 78.27, 424/78.08; 526/307

[56] References Cited

U.S. PATENT DOCUMENTS

| | | | |
|---|---|---|---|
| 3,308,020 | 3/1967 | Wolf et al. | 424/78.1 |
| 3,733,400 | 5/1973 | Orienille et al. | 424/78.1 |
| 3,787,474 | 1/1974 | Daniels et al. | 526/259 |
| 4,060,678 | 11/1977 | Steepler | 526/260 |
| 4,082,701 | 4/1978 | Fries et al. | 526/307 |
| 4,211,765 | 7/1980 | Johnson et al. | 424/78.1 |
| 4,311,799 | 1/1982 | Miyake et al. | 521/31 |
| 5,236,701 | 8/1993 | St. Pierre et al. | 424/78.1 |

FOREIGN PATENT DOCUMENTS 3001856  7/1981  Germany ................. 521/32

*Primary Examiner*—Thurman K. Page
*Assistant Examiner*—Peter F. Kulkosky
*Attorney, Agent, or Firm*—Phillips Moore Lempio & Finley

[57] ABSTRACT

The invention is concerned with novel ingestible cross-linked homopolymers having functional groups consisting of linear or branched amines, of the formula:

$$P-[NR(CH_2)_n]_m N(R)_2 \quad \text{or} \quad \text{(Ia)}$$

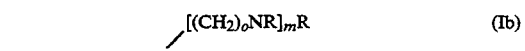

(Ib)

and their pharmaceutically acceptable salts of the formulae:

$$P-[N^+(R)_2(CH_2)_n]_m N^+(R)_3 \cdot (m+1)X^- \quad \text{and} \quad \text{(Ic)}$$

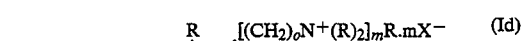

(Id)

wherein P(or POLYMER ||-) represents a hydrophobic, cross-linked and non-digestible homopolymer backbone; R is a hydrogen atom or a lower alkyl radical; $X^-$ is a pharmaceutically acceptable anion; m is an integer varying from 1 to 6 inclusive; and n, o and p are, independently, integers varying from 2 to 12 inclusive. The amine functionalized and cross-linked homopolymers of the invention are highly efficient adsorbents for bile acids and salts and can thus be used for reducing hypercholesterolemia in affected humans.

23 Claims, 2 Drawing Sheets

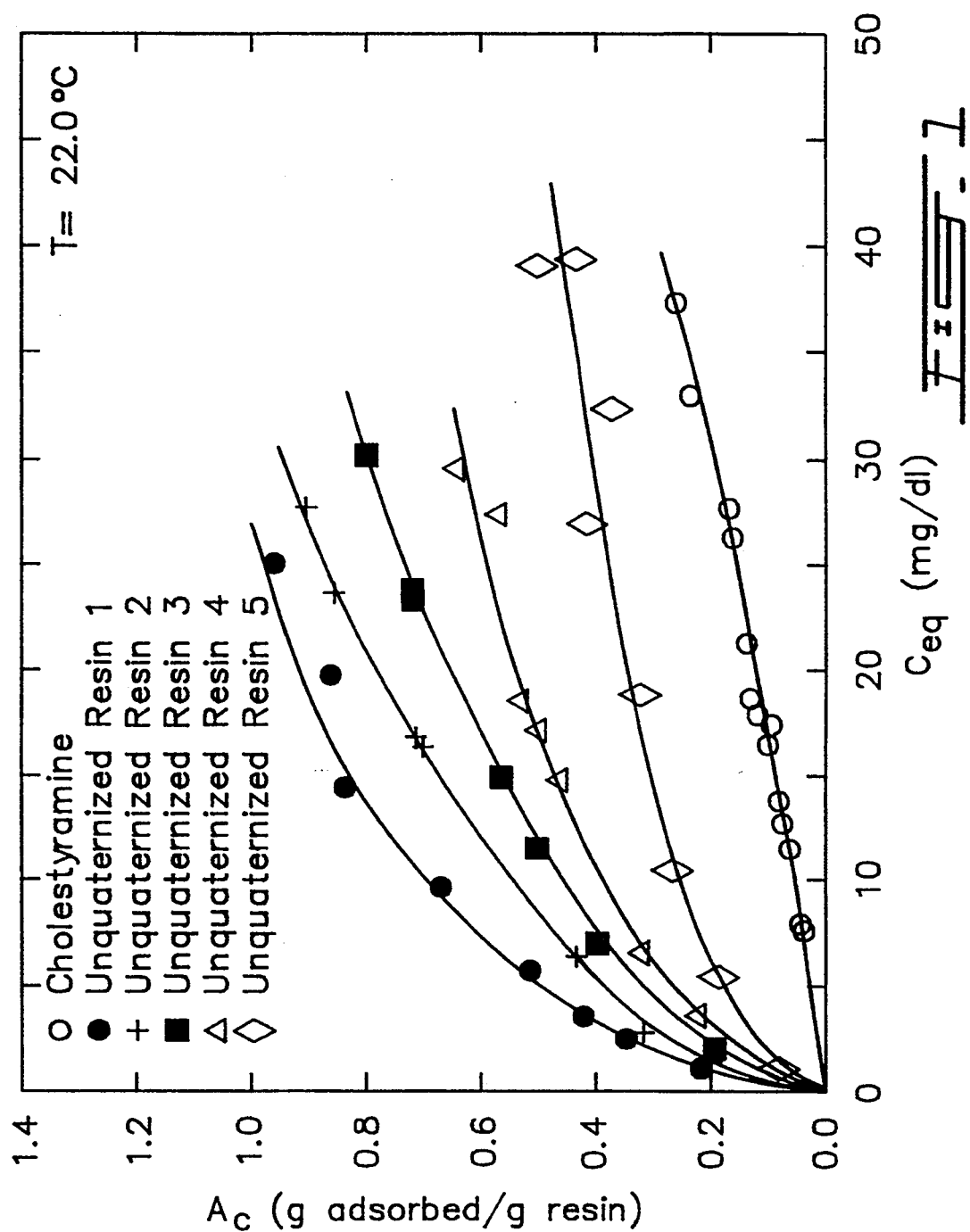

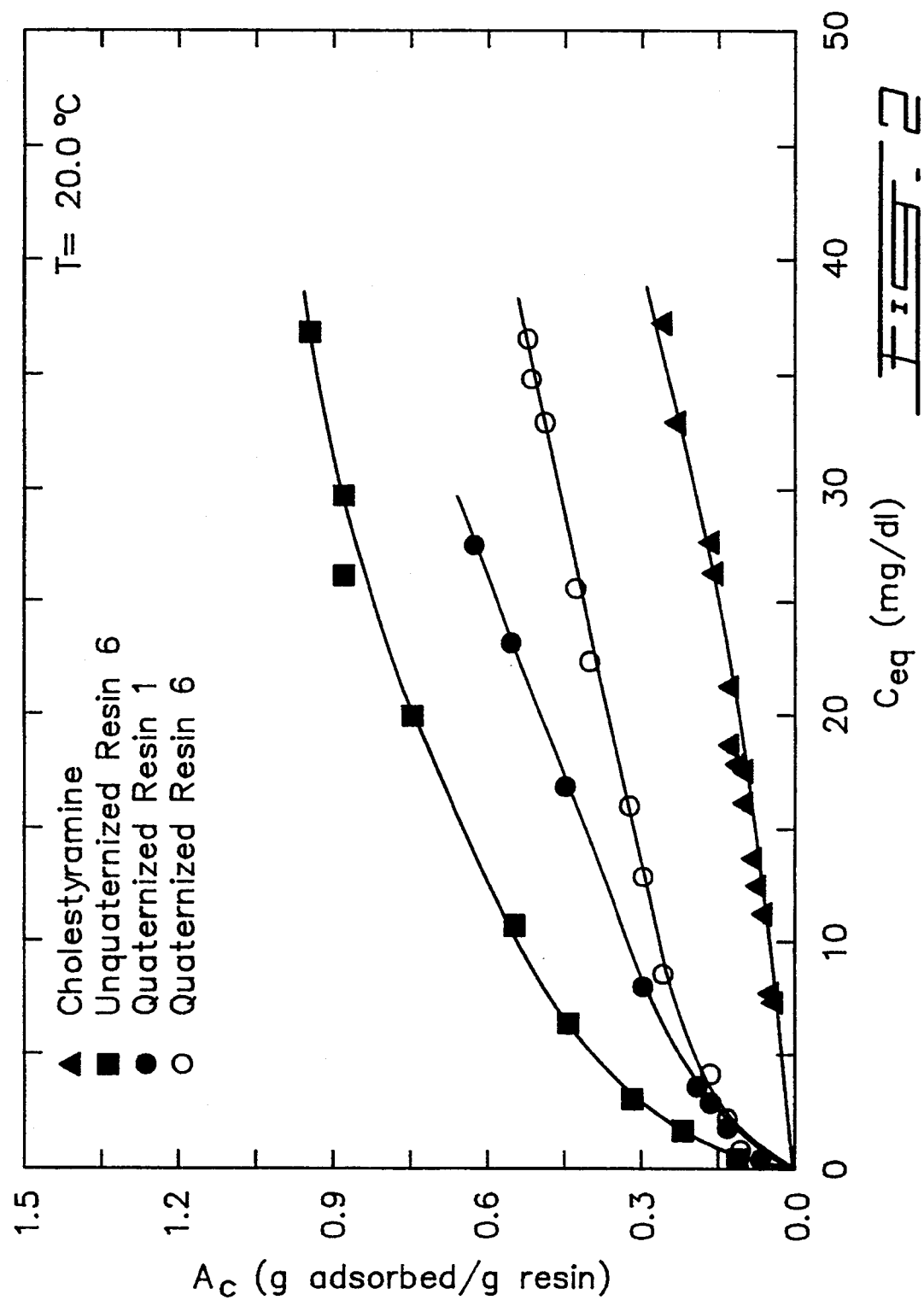

INGESTIBLE [HYDROPHOBIC] POLYMERIC AMINES USEFUL FOR LOWERING BLOOD CHOLESTEROL

RELATED APPLICATIONS

This application is a continuation-in-part of copending U.S. Ser. No. 07/381,988, filed Jul. 19, 1989, now U.S. Pat. No. 5,236,701.

BACKGROUND OF THE INVENTION

1. Field of the Invention

The present invention relates to novel ingestible amine functionalized and cross-linked homopolymers which are useful as adsorbents for bile salts. Note particularly, the invention is directed toward the treatment of hypercholesterolemia by removing through adsorption of the bile acids and sales from the small intestine, thereby increasing the catabolism of cholesterol in the liver with a concomitant decrease in the blood cholesterol level.

2. Related Art

All available evidence indicates that the incidence of higher than normal blood serum cholesterol levels in humans is associated with atheroslerosis and other hypercholesterolemic disease signs. Hypercholesterolemia, the leading cause of death in many countries, is presently treated by restricted and special dietary intake, inhibitation of cholesterol synthesis, accelerated catabolism and prevention of gastrointestinal adsorption. Increased catabolism of cholesterol can be achieved by the oral administration of bile salt binding agents, which has been widely used and well accepted.

Applicants have already described, in the aforementioned patent application, bile salt adsorbents which consist of amine functionalized homopolymers having a hydrophilic, cross-linked and non-digestible homopolymer backbone. These adsorbents are more hydrophilic than cholestyramine, the most widely used adsorbent for bile salts, and thus have better biocompatibility.

As discussed in the above patent application, for any medical applications, especially by oral administration, the hydrophilicity or water-swellability of a polymer material to be administrated is often considered as a major evaluation parameter because most of the human fluids have high water contents. Generally, the more water-swellable the polymer material is, the more biocompatible it will be.

SUMMARY OF THE INVENTION

Applicant has now found quite unexpectedly that highly efficient bile adsorbents exhibiting increased hydrophilicity cam be produced starting from a hydrophobic and cross-linked polymer backbone, by increasing the number of hydrophilic amines attached to the polymer backbone. As a result, not only is the hydrophilicity of the adsorbent increased, but also the number of adsorption sites per unit weight, that is, the adsorption capacity.

In accordance with the present invention, there is thus provided a novel cross-linked homopolymer having functional groups consisting of linear or branched amines, of the formula:

$$P\text{---}[NR(CH_2)_n]_m N(R)_2 \quad \text{or} \quad (Ia)$$

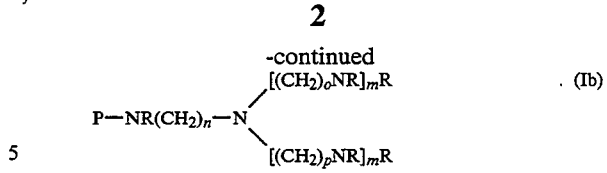

as well as the pharmaceutically acceptable salts thereof having the formulae:

$$P\text{---}[N^+(R)_2(CH_2)_n]_m N^+(R)_3 \cdot (m+1)X^- \quad \text{and} \quad (Ic)$$

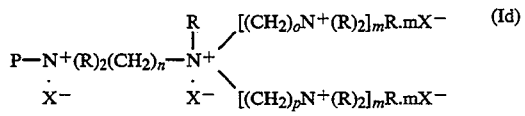

wherein:
- P (or POLYMER ||  - which designations are known in the art and are considered to be equivalent and are used interchangeably herein) represents a hydrophobic, cross-linked and non-digestible homopolymer backbone;
- R is a hydrogen atom or a lower alkyl radical;
- $X^-$ is a pharmaceutically acceptable anion;
- m is an integer varying from 1 to 6 inclusive; and
- n, o and p are, independently, integers varying from 2 to 12 inclusive.

As explained in Applicants aforementioned patent application, the polymer backbone to which the amino groups are chemically bonded must be cross-linked to prevent the adsorbent from diffusing from the digestive tract, as well as non-digestible to prevent the adsorbent from being broken down and absorbed into the body. A preferred polymer resin for use as backbone to which the amino groups can be attached is a cross-linked poly(p-chloromethylene styrene) resin. Such a resin is sold under the trade mark Bio-Beads S-X1 by BIO-RAD Laboratories of Richmond, Calif.

Particularly preferred amine-containing resins according to the invention are the homopolymers functionalized with linear amines of formula (Ia) and their protonated and quaternized derivatives of formula (Ic), in which R is a hydrogen atom or a methyl radical, m is 1 or 3, n is 2, 4, 6, 8 or 12, P represents a poly(p-methylene styrene) backbone and $X^-$ is a pharmaceutically acceptable anion, such as $Cl^-$, $I^-$ or $OH^-$ Among the homopolymers functionalized with branched amines of formula (Ib) and their protonated and quaternized derivatives of formula (Id), the preferred compounds are those in which R is a hydrogen atom or a methyl radical, m is 1, n, o and p are each 2, P represents a poly(p-methylene styrene) backbone and $X^-$ is a pharmaceutically acceptable anion.

The present invention also provides, in a further aspect thereof, a method of treating hypercholesterolemia in an affected human, which comprises administering to the affected human an effective amount of a bile salt adsorbent consisting of an amine functionalized and cross-linked homopolymer as defined above.

According to yet another aspect of the invention, there is provided a pharmaceutical composition for the treatment of hypercholesterolemia, which comprises as active ingredient an amine functionalized and cross-linked homopolymer as defined above, together with a pharmaceutically acceptable carrier therefor.

The amine-containing resins according to the invention not only exhibit high adsorption capacity but also high water-swellability, which render them suitable for clinical application.

Further features and advantages of the invention will become more readily apparent from the following non-limiting examples and the accompanying drawings.

BRIEF DESCRIPTION OF THE DRAWINGS

FIGS. 1 and 2 show the adsorption isotherms of compounds according to the invention for sodium glycocholate in aqueous 0.050M NaCl solution, at 22.0° C. and 20.0° C. respectively, compared with the adsorption isotherm of cholestyramine (used as reference adsorbent).

DETAILED DESCRIPTION OF THE INVENTION AND PREFERRED EMBODIMENTS

1. Preparation of Amine-Containing Resins 2.0 grams of Bio-Beads S-X1, a cross-linked poly(p-chloromethylene styrene) resin, and 10 ml of N,N-dimethylformamide were mixed in a 3-necked flask equipped with a mechanical stirrer, a condenser and a stopper. The resin was allowed to swell for 20 minutes before 30 ml of an alkylamine were added. Then the reaction was allowed to proceed for three successive periods of 2, 21 and 24 hours at room temperature, 60° C. and 71° C., respectively. The amine-containing resin thus obtained was purified by washing with ethanol in a Soxhlet extractor for 24 hours, then packed into a column and washed with distilled water for 24 hours. It was finally dried under vacuum for 3 days.

2. Protonation of the Amine-Containing Resins

The amine-containing resins were treated with dilute hydrochloric acid solution (0.2M) at room temperature to convert the free amine groups to positively charged organic ammonium groups. This can be done either in a column where dilute HCl passes through the column until the protonation is complete, or simply in a container where an excess amount of hydrochloric acid is in contact with the resin (standing or shaking). Then the excess hydrochloric acid was washed away with a large amount of distilled water until the resin is neutral.

3. Quaternization of the Amine-Containing Resins

A 250 ml 3-necked flask equipped with a mechanical stirrer, a condenser and a thermometer was immersed in a water bath. 1.6 grams of the amine-containing resin prepared above, 5.5 grams of $KHCO_3$ and 30 ml methanol were added. After 2 hours of stirring at 25° C., 40 ml methyl iodide were added, The reaction was maintained at 34° C. for 5 days. The final product was washed with methanol in a column before it was converted to chloride form by washing with concentrated sodium chloride. It was treated with distilled water again to remove any remaining salt and then dried under vacuum.

4. Characterization of the Adsorbents

The products were characterized both qualitatively by infrared spectroscopy and quantitatively by acid-base back titration. FT-IR measurements confirmed that the various amines had been chemically attached to the polymer backbone. From acid base back titration, it was found that the amine functionalities of the resins were in the range of 5-8 mmol/g (dry).

5. Adsorption Studies

A bile salt solution with a concentration of about 50 mg/dl was prepared with 0.05M NaCl aqueous solution. Into bottles of different sizes (2-50 ml), about 5-15 mg of the resin to be tested was weighed. Then different volumes of bile salt solution (1-30 ml) were added into the bottles. By changing the volumes of the bile salt solution added, a whole range of bile salt equilibrium concentration was easily reached. They were shaken at room temperature (15°-25° C.) for more than 2 hours. Then they were filtered and the clear solutions were analyzed by High Performance Liquid Chromatography (HPLC).

Example 1

An amine-containing resin was prepared as described above by grafting onto the Bio-Beads S-X1 backbone ethylenediamine and was then converted to the hydrochloride form by washing with dilute aqueous HCl. This material, designated "unquaternized resin 1", was shaken with a $Na^+$-glycocholate solution in 0.05 NaCl solution at initial bile salt concentration of 30-60 mg/dl and at room temperature, for more than 2 hours. The amount of $Na^+$-glycocholate adsorbed was measured by HPLC as described above. The adsorption isotherm is shown in FIG. 1. At an equilibrium concentration of 20 mg/dl, this resin adsorbed 0.91 gram of $Na^+$-glycocholate per gram of resin.

Example 2

Example 1 was repeated except that 1,4-diaminobutane, instead of ethylene diamine, was grafted onto the Bio-Beads S-X1 backbone. The product obtained, designated "unquaternized resin 2", adsorbed 0.79 gram of $Na^+$-glycocholate per gram of resin at an equilibrium concentration of 20 mg/dl. The adsorption isotherm is shown in FIG. 1.

Example 3

Example 1 was repeated except that 1,6-hexanediamine, instead of ethylene diamine, was grafted onto the Bio-Beads S-X1 backbone. The product obtained, designated "unquaternized resin 3", adsorbed 0.67 gram of $Na^+$-glycocholate per gram of resin at an equilibrium concentration of 20 mg/dl. The adsorption isotherm is shown in FIG. 1.

Example 4

Example 1 was repeated except that 1,8-diaminooctane, instead of ethylene diamine, was grafted onto the Bio-Beads S-X1 backbone. The product obtained, designated "unquaternized resin 4", adsorbed 0.55 gram of $Na^+$-glycocholate per gram of resin at an equilibrium concentration of 20 mg/dl. The adsorption isotherm is shown in FIG. 1.

Example 5

Example 1 was repeated except that 1,12-diaminododecane, instead of ethylene diamine, was grafted onto the Bio-Beads S-X1 backbone. The product obtained, designated "unquaternized resin 5", adsorbed 0,35 gram of $Na^+$-glycocholate per gram of resin at an equilibrium concentration of 20 mg/dl. The adsorption isotherm is shown in FIG. 1.

Example 6

Example 1 was repeated except that triethylenetetraamine, instead of ethylene diamine, was grafted onto the Bio-Beads S-X1 backbone. The product obtained, designated "unquaternized resin 6", adsorbed 0.75 gram of $Na^+$-glycocholate per gram of resin at an equilibrium concentration of 20 mg/dl. The adsorption isotherm is shown in FIG. 2.

Example 7

Example 1 was repeated except that the amine-containing resin was quaternized with methyl iodide and then was converted to chloride form by washing with concentrated sodium chloride solution. The product obtained, designated "quaternized resin 1", adsorbed 0.50 gram of $Na^+$-glycocholate per gram of resin at an equilibrium concentration of 20 mg/dl. The adsorption isotherm is shown in FIG. 2.

Example 8

Example 6 was repeated except that the amine-containing resin was quaternized and converted in the manner described in Example 7. The product obtained, designated "quaternized resin 6", adsorbed 0.35 gram of $Na^+$-glycocholate per gram of resin at an equilibrium concentration of 20 mg/dl. The adsorption isotherm is shown in FIG. 2.

Example 9

Example 1 was repeated except that tris(2-aminoethyl) amine, instead of ethylene diamine was grafted onto the Bio-Beads S-X1 backbone. The product obtained, designated "unquaternized resin 7", adsorbed 0.75 gram of $Na^+$-glycocholate per gram of resin at an equilibrium concentration of 20 mg/dl.

The adsorption capacities of the amino-containing resins prepared in Examples 1 through 9 are summarized in the following Table:

TABLE 1

| Ex. No. | Product Designation | Structure | Adsorption Capacity (*) |
|---|---|---|---|
| 1 | Unquaternized Resin 1 | $P-N^+H_2(CH_2)_2N^+H_3.2Cl^-$ | 0.91 |
| 2 | Unquaternized Resin 2 | $P-N^+H_2(CH_2)_4N^+H_3.2Cl^-$ | 0.79 |
| 3 | Unquaternized Resin 3 | $P-N^+H_2(CH_2)_6N^+H_3.2Cl^-$ | 0.67 |
| 4 | Unquaternized Resin 4 | $P-N^+H_2(CH_2)_8N^+H_3.2Cl^-$ | 0.55 |
| 5 | Unquaternized Resin 5 | $P-N^+H_2(CH_2)_{12}N^+H_3.2Cl^-$ | 0.35 |
| 6 | Unquaternized Resin 6 | $P-[N^+H_2(CH_2)_2]_3N^+H_3.4Cl^-$ | 0.75 |
| 7 | Quaternized Resin 1 | $P-N^+(CH_3)_2(CH_2)_2N^+(CH_3)_3.2Cl^-$ | 0.50 |
| 8 | Quaternized Resin 6 | $P-[N^+(CH_3)_2(CH_2)_2]_3N^+(CH_3)_3.4Cl^-$ | 0.35 |
| 9 | Unquaternized Resin 7 | $P-N^+H_2(CH_2)_2-\overset{\overset{H}{\mid}}{\underset{\underset{Cl^-}{\mid}}{N^+}}\diagup^{(CH_2)_2N^+H_3.Cl^-}_{\diagdown_{(CH_2)_2N^+H_3.Cl^-}}$ $Cl^-$ | 0.75 |

(*) gram of sodium glycocholate adsorbed per gram of resin (at an equilibrium concentration of 20 mg/dl).

As may be seen from FIG. 1, the adsorption behavior of the amine-containing resins is strongly dependent on the length of the hydrophobic spacer $(CH_2)_n$. As it is also apparent from FIGS. 1 and 2, all the resins with multiple amine functional groups exhibit adsorption capacities superior to that of cholestyramine.

The embodiments of the invention, in which an exclusive property or privilege is claimed, are defined as follows:

1. A pharmaceutical composition for the treatment of hypercholesterolemia, said composition comprising:
   a) a water-swellable, amine homopolymer selected from the group consisting of those having the chemical formula:

POLYMER $(NR(CH_2)_n)_m N(R)_2$;  (Ia)

POLYMER $NR(CH_2)_n-N\diagup^{((CH_2)_oNR)_mR}_{\diagdown_{((CH_2)_pNR)_mR}}$ ;  (Ib)

POLYMER $(N^+(R)_2(CH_2)_n)_m N^+(R)_3.(m + 1)X^-$; and  (Ic)

POLYMER $N^+(R)_2(CH_2)_n-\overset{\overset{R}{\mid}}{\underset{\underset{X^-}{\mid}}{N^+}}\diagup^{((CH_2)_oN^+(R)_2)_m R.mX^-}_{\diagdown_{((CH_2)_pN^+(R)_2)_m R.mX^-}}$  (Id)

where compounds (1c) and (1d) are the pharmaceutically acceptable salts of (1a) and (1b) as an active ingredient;
wherein POLYMER ||- represents a hydrophobic, covalently cross-linked, non-digestible homopolymer backbone, R is hydrogen or lower alkyl, $X^-$ is a pharmaceutically acceptable anion, m is an integer of 1 to 6, and n, o and p are each independently integers between 2 to 12; and b) a pharmaceutically acceptable carrier, wherein said active ingredient is present in an anticholesterolemic effective amount.

2. A pharmaceutical composition for the treatment of hypercholesterolemia, said composition comprising:

a) an anti-hypercholesterolemic effective amount of a water-swellable, amine homopolymer selected from the group consisting of those having the chemical formula:

POLYMER $(NR(CH_2)_n)_m N(R)_2$;  (Ia)

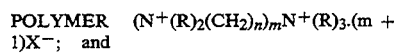  (Ib)

POLYMER $(N^+(R)_2(CH_2)_n)_m N^+(R)_3 \cdot (m + 1)X^-$; and  (Ic)

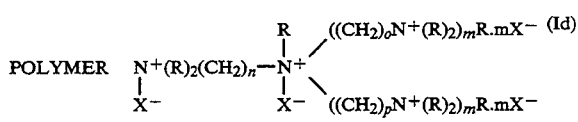  (Id)

where compounds (1c) and (1d) are the pharmaceutically acceptable salts of (1a) and (1b) as an active ingredient;

wherein

POLYMER ||- represents a hydrophobic, covalently cross-linked, non-digestible homopolymer backboner of poly (p-methylenestyrene) as an effective ingredient;

R is hydrogen or lower alkyl, $X^-$ is a pharmaceutically acceptable anion, m is an integer of 1 to 6, and n, o and p are each independently integers between 2 to 12; and a pharmaceutical acceptable carrier.

3. A method of treating hypercholesterolemia in a subject comprising administering to a subject in need of such treatment an anti-hypercholesterolemic effective amount of a water-swellable, amine homopolymer selected from the group consisting of those having the chemical formula POLYMER $(NR(CH_2)_n)_m N(R)_2$,  (Ia)

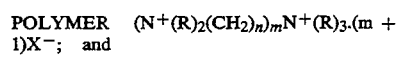  (Ib)

POLYMER $(N^+(R)_2(CH_2)_n)_m N^+(R)_3 \cdot (m + 1)X^-$; and  (Ic)

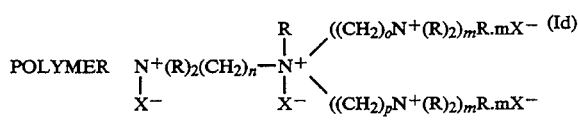  (Id)

where compounds (1c) and (1d) are the pharmaceutically acceptable salts of compounds (1a) and (1b), wherein POLYMER ||- is a hydrophobic, water-swellable, non-digestible homopolymer backbone, R is hydrogen or lower alkyl, $X^-$ is a pharmaceutically acceptable anion, m is an integer of 1 to 6, and n, o and p are each independent integers between 2 to 12.

4. A method of treating hypercholesterolemia in a subject comprising administering to a subject in need of such treatment an anti-hypercholesterolemic effective amount of a water-swellable, amine homopolymer selected from the group consisting of those having the chemical formula POLYMER $(NR(CH_2)_n)_m N(R)_2$,  (Ia)

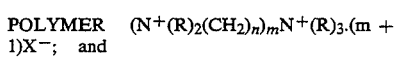  (Ib)

POLYMER $(N^+(R)_2(CH_2)_n)_m N^+(R)_3 \cdot (m + 1)X^-$; and  (Ic)

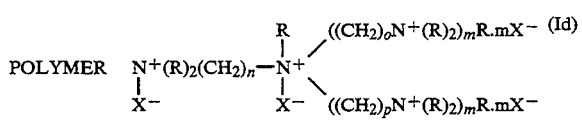  (Id)

where compounds (1c) and (1d) are the pharmaceutically acceptable salts of compounds (1a) and (1b), wherein POLYMER ||- is a hydrophobic, water-swellable, non-digestible homopolymer backbone, of poly (p-methylenestyrene);

R is hydrogen or lower alkyl, $X^-$ is a pharmaceutically acceptable anion, m is an integer of 1 to 6, and n, o and p are, each independent integers between 2 to 12.

5. The pharmaceutical composition of claim 2, wherein the active ingredient is a water-swellable, amine homopolymer having the chemical formula (1a) or a pharmaceutically acceptable salt thereof having the chemical formula (1c), wherein POLYMER || - is a poly(p-methylene styrene) backbone, wherein said active ingredient is present in an anticholesterolemic effective amount.

6. The pharmaceutical composition of claim 2, wherein the active ingredient is a water-swellable, amine homopolymer having the chemical formula (1b) or a pharmaceutically acceptable salt thereof having the chemical formula (1d), wherein R is hydrogen or methyl;

m is 1; and n, o and p are each 2.

7. The pharmaceutical composition of claim 2, wherein the active ingredient is a water-swellable, amine homopolymer having the chemical formula (1b) or a pharmaceutically acceptable salt thereof having the chemical formula (1d), wherein POLYMER || - is a poly(p-methylene styrene) backbone.

8. The pharmaceutical composition of claim 2, wherein the active ingredient is a water-swellable, amine homopolymer having the chemical formula

POLYMER ||-NH—(CH$_2$)$_2$NH$_2$ or a pharmaceutically acceptable salt thereof having the chemical formula POLYMER ||-(N$^+$H$_2$(CH$_2$)$_2$N$^+$(H)$_3$·2X$^-$ or

POLYMER ||-(N$^+$(CH$_3$)$_2$(CH$_2$)$_2$N$^+$(CH$_3$)$_3$·2X$^-$, wherein POLYMER || - is a poly(p-methylene styrene) backbone.

9. The pharmaceutical composition of claim 2, wherein the active ingredient is a water-swellable, amine homopolymer having the chemical formula

POLYMER ||-NH(CH$_2$)$_4$NH$_2$ or a pharmaceutically acceptable salt thereof

POLYMER ||-N$^+$(CH$_3$)$_2$(CH$_2$)$_4$N$^+$(CH$_3$)$_3$·2X$^-$, wherein POLYMER || - is a poly(p-methylene styrene) backbone.

10. The pharmaceutical composition of claim 2, wherein the active ingredient is a water-swellable, amine homopolymer having the chemical formula

POLYMER ||-NH(CH$_2$)$_6$NH$_2$ or a pharmaceutically acceptable salt thereof having the chemical formula POLYMER ||-N$^+$H$_2$(CH$_2$)$_6$N$^+$H$_3$·2X$^-$ or

POLYMER ||-N$^+$(CH$_3$)$_2$(CH$_2$)$_6$ N$^+$(CH$_3$)$_3$·2X$^-$, wherein POLYMER || - is a poly(p-methylene styrene) backbone.

11. The pharmaceutical composition of claim 2, wherein the active ingredient is a water-swellable, amine homopolymer having the chemical formula

POLYMER ||-NH(CH$_2$)$_8$NH$_2$ or a pharmaceutically acceptable salt thereof having the chemical formula POLYMER ||-N$^+$H$_2$(CH$_2$)$_8$N$^+$H$_3$·2X$^-$ or

POLYMER ||-N$^+$(CH$_3$)$_2$(CH$_2$)$_8$N$^+$(CH$_3$)$_3$·2X$^-$, wherein POLYMER || - is a poly(p-methylene styrene) backbone.

12. The pharmaceutical composition of claim 2, wherein the active ingredient is a water-swellable, amine homopolymer having the chemical formula

POLYMER ||-NH(CH$_2$)$_{12}$NH$_2$ or a pharmaceutically acceptable salt thereof having the chemical formula POLYMER ||-N$^+$H$_2$(CH$_2$)$_{12}$N$^+$H$_3$·2X$^-$ or

POLYMER ||-N$^+$(CH$_3$)$_{[2]3}$(CH$_2$)$_{12}$ N$^+$(CH$_3$)$_3$·2X$^-$, wherein POLYMER || - is a poly(p-methylene styrene) backbone.

13. The pharmaceutical composition claim 2, wherein the active ingredient is a water-swellable, amine homopolymer having the chemical formula

POLYMER ||-NH(CH$_2$)$_2$)$_3$NH$_2$ or a pharmaceutically acceptable salt thereof having the chemical formula POLYMER ||-(N$^+$H$_2$(CH$_2$)$_2$)$_3$N$^+$H$_3$·4X$^-$ or

POLYMER ||-(N$^+$(CH$_3$)$_2$(CH$_2$)$_2$)$_3$N$^+$(CH$_3$)$_3$·4X$^-$, wherein POLYMER || - is a poly(p-methylene styrene) backbone, and X$^-$ is a pharmaceutically acceptable anion.

14. The method of claim 3, wherein
the homopolymer administered to the subject comprises a homopolymer having the chemical formula (1a) or a pharmaceutically acceptable salt thereof having the chemical formula (1c), wherein POLYMER || - is a poly(p-methylene styrene) backbone.

15. The method of claim 4, wherein
the homopolymer administered to the subject comprises a homopolymer having the chemical formula (1b) or a pharmaceutically acceptable salt thereof having the chemical formula (1d), wherein R is hydrogen or methyl, m is 1, and n, o and p are each 2.

16. The method of claim 4, wherein
the homopolymer administered to the subject comprises a homopolymer having the chemical formula (1b) or a pharmaceutically acceptable salt thereof having the chemical formula (1d), wherein POLYMER || - is poly(p-methylene styrene) backbone.

17. The method of claim 4, wherein
the homopolymer administered to the subject comprises a homopolymer having the chemical formula

POLYMER ||-NH—(CH$_2$)$_2$ NH$_2$ or a pharmaceutically acceptable salt thereof having the chemical formula or

POLYMER ||-(N$^+$(H)$_2$(CH$_2$)$_2$N$^+$(H)$_3$·2X$^-$

POLYMER ||-(N$^+$(CH$_3$)$_2$(CH$_2$)$_2$N$^+$(CH$_3$)$_3$·2X$^{-s}$
wherein POLYMER || - is a poly(p-methylene styrene) backbone.

18. The method of claim 4, wherein
the homopolymer administered to the subject comprises a homopolymer having the chemical formula

POLYMER ||-NH(CH$_2$)$_4$NH$_2$ or a pharmaceutically acceptable salt thereof

POLYMER ||-N$^+$H$_2$(CH$_2$)$_4$N$^+$H$_3$·2X$^-$ or

POLYMER ||-N$^+$(CH$_3$)$_2$(CH$_2$)$_4$N$^+$(CH$_3$)$_3$·2X$^-$, wherein POLYMER || - is a poly(p-methylene styrene) backbone.

19. The method of claim 4, wherein
the homopolymer administered to the subject comprises a homopolymer having the chemical formula

POLYMER ||-NH(CH$_2$)$_6$NH$_2$ or a pharmaceutically acceptable salt thereof having the chemical formula POLYMER ||-N$^+$H$_2$(CH$_2$)$_6$N$^+$H$_3$·2X$^-$ or

POLYMER ||-N$^+$(CH$_3$)$_2$(CH$_2$)$_6$N$^+$(CH$_3$)$_3$·2X$^-$, wherein POLYMER ||- is a poly(p-methylene styrene) backbone.

20. The method of claim 4, wherein
the homopolymer administered to the subject comprises a homopolymer having the chemical formula

POLYMER ||-NH(CH$_2$)$_8$NH$_2$ or a pharmaceutically acceptable salt thereof having the chemical formula POLYMER ||- N$^+$H$_2$(CH$_2$)$_8$N$^+$H$_3$·2X$^-$ or

POLYMER ||- N$^+$(CH$_3$)$_2$(CH$_2$)$_8$N$^+$(CH$_3$)$_3$·2X$^-$, wherein POLYMER ||- is a poly(p-methylene styrene) backbone.

21. The method of claim 4, wherein
the homopolymer administered to the subject comprises a homopolymer having the chemical formula

POLYMER ||-NH(CH$_2$)$_{12}$NH$_2$ or a pharmaceutically acceptable salt thereof having the chemical formula POLYMER ||-(N$^+$H$_2$(CH$_2$)$_{12}$N$^+$H$_3$2X$^-$ or

POLYMER ||-(N$^+$(CH$_3$)$_2$(CH$_2$)$_{12}$N$^+$(CH$_3$)$_3$·2X$^-$, wherein POLYMER ||- is a poly(p-methylene styrene) backbone.

22. The method of claim 4, wherein
the homopolymer administered to the subject comprises a homopolymer having the chemical formula

POLYMER ||-NH(CH$_2$)$_2$)$_3$NH$_2$ or a pharmaceutically acceptable salt thereof having the chemical formula POLYMER ||-(N$^+$H$_2$(CH$_2$)$_2$)$_3$N$^+$H$_3$·4X$^-$ or

POLYMER ||-(N$^+$(CH$_3$)$_2$(CH$_2$)$_2$)$_3$N$^+$(CH$_3$)$_3$·4X$^-$, wherein POLYMER ||- is a poly(p-methylene styrene) backbone.

23. The method of claim 4, wherein the subject is a human being.

* * * * *